US006319513B1

(12) United States Patent
Dobrozsi

(10) Patent No.: US 6,319,513 B1
(45) Date of Patent: Nov. 20, 2001

(54) ORAL LIQUID MUCOADHESIVE COMPOUNDS

(75) Inventor: Douglas Joseph Dobrozsi, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/361,533

(22) Filed: Jul. 27, 1999

Related U.S. Application Data
(60) Provisional application No. 60/097,578, filed on Aug. 24, 1998.

(51) Int. Cl.[7] .................................................. A61F 13/02
(52) U.S. Cl. ........................................... 424/434; 424/435
(58) Field of Search ..................................... 424/434, 435

(56) References Cited

U.S. PATENT DOCUMENTS

| 3,352,752 | 11/1967 | Puetzer et al. ..................... 167/55 |
| 4,427,681 | 1/1984 | Munshi .................................. 424/260 |
| 5,047,244 | 9/1991 | Sanvordeker et al. ............. 424/435 |

(List continued on next page.)

FOREIGN PATENT DOCUMENTS

| 0062578 | 6/1984 | (EP) . |
| 0245855 | 11/1987 | (EP) . |
| 0 517 274 A1 | 12/1992 | (EP) . |
| 0526862 | 2/1996 | (EP) . |
| 2346017 | 10/1977 | (FR) . |
| 51142524 | 12/1976 | (JP) . |
| 080056 | 10/1982 | (RO) . |
| 076076 | 5/1983 | (RO) . |
| WO 91/06289 | 5/1991 | (WO) . |
| WO 92/09286 | 6/1992 | (WO) . |
| WO 96/20696 | 7/1996 | (WO) . |
| WO 96/25153 | 8/1996 | (WO) . |
| WO 96/40086 | 12/1996 | (WO) . |
| WO 97/12600 | 4/1997 | (WO) . |

OTHER PUBLICATIONS

Kennikoski, A., et al., "The Effects of Some Tablet Film Coatings on the Adherence of Drug Products to the Isolated Porcine Oesophagus", Pharmaceutica Fennica vol. 3, No. (2) 1984, pp. 75–83.

Formula for Antidiarrheal Oral Suspension No. 426, R. T. Vanderbilt Company, Inc., Specialties Department.

Label of Sonne's #7, Adsorbent Aid in Detoxification and Intestinal Purification via Alimentary Canal, distributed by Sonne's Organic Foods, Inc., Kansas City MO 64142.

Label description of Body Essential Silica Gel manufactured by Anton Huebner GmbH & Co., Ehrenkirchen, Germany, distributed by Nature Works, a Div.Of ABKIT, Inc., NY.

Advertisement depicting Silicol and translated description thereof, manufactured by Saguna GmbH, Germany.

(List continued on next page.)

Primary Examiner—Carlos Azpuru
(74) Attorney, Agent, or Firm—Betty J. Zea

(57) ABSTRACT

The present invention relates to a per oral, oral, or intranasal pharmaceutical mucoretentive, aqueous liquid composition comprising from about 2% to about 50%, by weight of the composition, of colloidal particles of silica, titanium dioxide, clay, and mixtures thereof and a safe and effective amount of a pharmaceutical active selected from the group consisting of analgesics, decongestants, expectorants, antitussives, antihistamines, sensory agents, gastrointestinal agents, and mixtures thereof; wherein the composition has a sedimentation volume ratio of greater than about 0.90 and wherein the triggered viscosity ratio of the composition is at least about 1.2. The present invention further relates to a method of coating the alimentary canal or nasal mucosa, in particular to a method of preventing or treating symptoms of upper respiratory tract infections or upper respiratory tract tissue irritation or damage, by administering a safe and effective amount of the above composition.

24 Claims, 1 Drawing Sheet

U.S. PATENT DOCUMENTS

| | | | |
|---|---|---|---|
| 5,244,667 | 9/1993 | Hagiwara et al. | 424/409 |
| 5,352,681 | 10/1994 | Wittebrood et al. | 514/166 |
| 5,458,879 | 10/1995 | Singh et al. | 424/400 |
| 5,464,828 | 11/1995 | Katayama et al. | 514/60 |
| 5,466,440 | 11/1995 | Ruddy et al. | 424/9.411 |
| 5,554,379 | 9/1996 | Cuca et al. | 424/439 |
| 5,554,380 | 9/1996 | Cuca et al. | 424/441 |
| 5,585,108 | 12/1996 | Ruddy et al. | 424/434 |
| 5,670,163 | 9/1997 | Cuca et al. | 424/439 |
| 5,672,356 | 9/1997 | Rault et al. | 424/468 |

OTHER PUBLICATIONS

"Gastrointestinal Protectives and Adsorbents", Goodman and Gilman's The Pharmacological Basis of Therapeutics, Seventh Edition, 1985, pp. 949.

Erös, I. et al., "Use of Colloidal Silicon Dioxide in Paharmaceutical Technology" [A kolloid sziliciumdioxid felhasználása a gyógyszertechnológiában], Gyógyszerészet 19 (1975), pp. 290–296.

Sherriff, M., et al., "Rheological and Drug Release Properties of Oil Gels Containing Colloidal Silicon Dioxide", Journal of Pharmaceutical Sciences vol. 68, No. 7, Jul. 1979, pp. 842–845.

Ciullo, P.A., "Rheological Properties of Magnesium Aluminum Silicate/xanthan Gum Dispersions", J. Soc. Cosmet. Chem., 32, Sep./Oct. 1981, pp. 275–285.

Ponchel, G., et al., "Mucoadhesion of Colloidal Particulate Systems in the Gastro–intestinal Tract", European Journal of Pharmaceutics and Biopharmaceutics 44 (1997), pp. 25–31.

Rossi, S., et al., "A Rheometric Method for Assessing the Sucralfate–Mucin Interaction", Eur. J. Pharm. Biopharm 40 (3) (1994), pp. 179–182.

Droy–Lefaix, M.T. "Smectite and the Intestinal Mucous Barrier" [Smectite et barrière muqueuse intestinale] [Complete source not given] Current events, pp. 411–420.

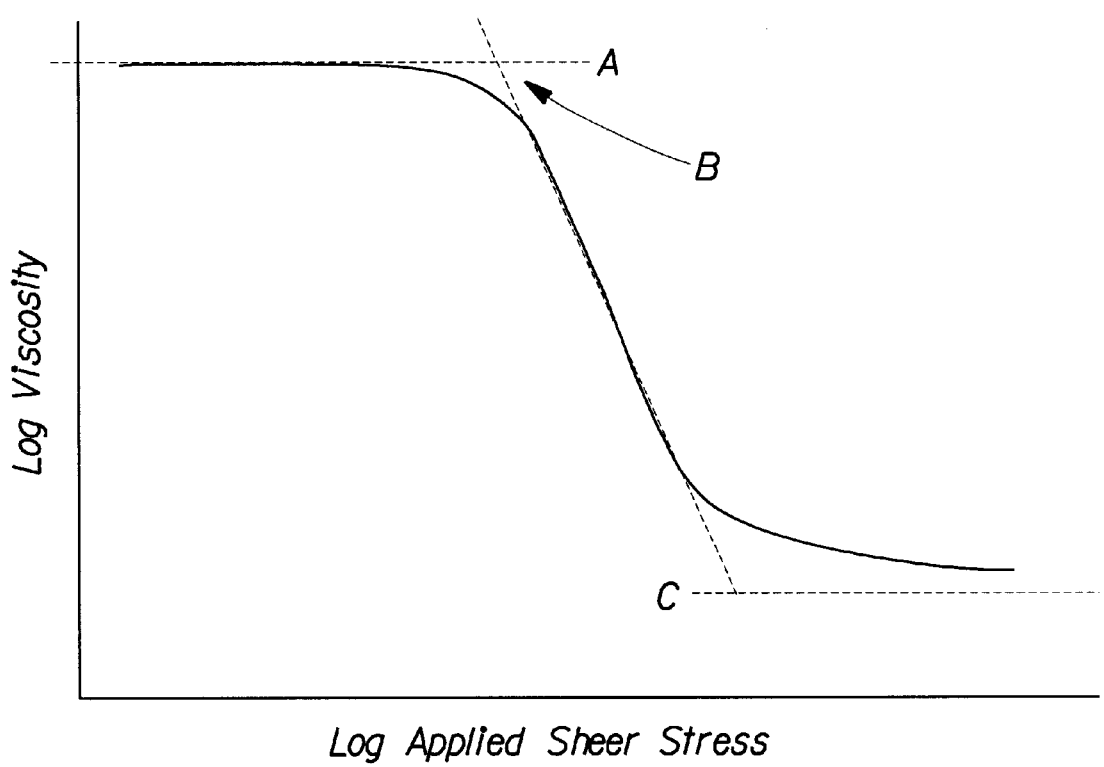

ORAL LIQUID MUCOADHESIVE COMPOUNDS

CROSS-REFERENCE TO RELATED APPLICATIONS

This application claims the benefit of US Provisional Application No. 60/097,578, filed Aug. 24, 1998.

TECHNICAL FIELD

The present invention relates to oral liquid pharmaceutical mucoadhesive compositions.

BACKGROUND OF THE INVENTION

Mucoadhesion has been a technology of great interest to pharmaceutical formulators and drug delivery scientists for many years. "Adhesion" refers to the relationship between two bodies, an adhesive and a substrate (both existing as condensed phases), when they are held together for an extended period of time by interfacial forces. Patrick R. L.: Introduction. In: *Treatise on Adhesion and Adhesives*, Volume 1: Theory. R. L. Patrick, Editor Marcel Dekker Inc. New York, 1966, pp. 1–7. An "adhesive" is a substance capable of holding materials together by surface attachment. The establishment of an adhesive bond between two materials leads to a reduction in the total surface energy in the system because two free surfaces are replaced by one new surface. "Bioadhesion" implies that at least one of the surfaces is of biological origin. When the surface is the adherent mucus layer covering one of the mucosal epithelia, such as the inside of the gastrointestinal tract, nasal tract, or vaginal cavity, the term "mucoadhesion" is used.

Mucoadhesive materials are useful in a wide variety of applications, particularly in pharmaceutical compositions. Mucoadhesive pharmaceutical compositions can provide prolonged and improved coating and protection of the mouth, esophagus, oropharynx, and/or stomach to inhibit irritation and/or accelerate healing of inflamed or damaged tissue. Furthermore, sustained or prolonged coating provides a matrix to deliver therapeutic agents to mucosal tissues at higher concentrations for higher efficacy, lower side effects, and/or sustained release of the active agent.

Compositions of the present invention are either directly applied to the mucosa or are administered as a per oral liquid suspension. Accordingly, there is a need to identify formulations that successfully and truly adhere to the gastrointestinal mucosa.

Virtually all of the prior art mucoadhesive systems require polymers to provide the mucoadhesive benefit. For example U.S. Pat. No. 5,458,879, Singh et al., issued Oct. 17, 1995, teaches solid dissolvable oral pharmaceutical mucoadhesive vehicle compositions which comprise from about 0.05 to about 20% of a water-soluble mucoadhesive polymer selected from the group consisting of poly(ethylene oxide), poly(ethylene glycol), poly(vinyl alcohol), poly(vinyl pyrrolidine), poly(acrylic acid), poly(hydroxy ethyl methacrylate), hydroxyethyl ethyl cellulose, hydroxy ethyl cellulose and chitosan and mixtures thereof, and also preferably comprise one or more pharmaceutical actives, preferably a cough/cold active, at a level of from about 0.01% to about 50%.

Other references teaching mucoadhesive polymer systems include: EP 526,862, Esposito et al., published Feb. 14, 1996, Vectorpharma; WO 91/06289, Sanvordeker, et al., published May 16, 1991 Watson Labs.; U.S. Pat. No. 3,352,752, Puetzer, et al., issued Nov. 14, 1967; WO 92/21325, Fouche, published Dec. 10, 1992 Union Metropolltaine; U.S. Pat. No. 5,225,196, Robinson, issued Jul. 6, 1993; Columbia Laboratories; WO 92/09286, Davis et al., published Jun. 11, 1992, Beecham Group PLC; U.S. Pat. No. 4,427,681, Munshi et al., issued Jan. 24, 1984, RVI; WO 96/20696, Ruddy et al., published Jul. 11, 1996, Eastman Kodak; U.S. Pat. No. 5,858,108, Ruddy et al., issued Dec. 17, 1996, Nanosystems; EP 062,578, Bodin et al., published Jun. 20, 1984, Laboratories Human-Pharm; WO 92/12600, Meignant, published Apr. 10, 1997.

The inventors have surprisingly discovered that certain pharmaceutical materials (titanium dioxide, silicon dioxide, and/or clays) provide mucoadhesive effects. When formulated in certain proportions in aqueous colloidal dispersions with drug actives, and in the form of a flowable liquid, these materials are able to interact with glycoprotein, especially mucin, transforming into a viscous gel, to become effective mucoadhesive systems. This adhesion occurs even though the formulation does not contain any material previously considered to be mucoadhesive, e.g. polymers. These formulations of the present invention provide prolonged and improved coating and protection of the mouth, esophagus, oropharynx, and/or the stomach for relief of irritation, pain and discomfort associated with ailments of the gastrointestinal tract such as laryngopharyngitis ("sore throat") and other upper respiratory tract infections/conditions/irritations. Furthermore, these formulations can provide a matrix to deliver an active ingredient in more intimate, concentrated, and sustained contact with the irritated area.

SUMMARY OF THE INVENTION

The present invention relates to a mucoretentive pharmaceutical, aqueous liquid composition comprising:
(a) from about 2% to about 50%, by weight of the composition, of colloidal particles selected from the group consisting of silica, titanium dioxide, clay, and mixtures thereof; and
(b) a safe and effective amount of a pharmaceutical active selected from the group consisting of analgesics, decongestants, expectorants, antitussives, antihistamines, bronchodilators, topical anesthetics, sensory agents, oral care agents, miscellaneous respiratory agents, gastrointestinal agents, and mixtures thereof;
wherein the composition has a sedimentation volume ratio of greater than about 0.90 and wherein the triggered viscosity ratio of the composition is at least about 1.2. The present invention further relates to a method of coating the alimentary canal (nasal cavity, oral cavity, esophagus, stomach, and small intestine), in particular to a method of preventing or treating symptoms of upper respiratory tract infections or upper respiratory tract tissue irritation or damage, by administering a safe and effective amount of the above composition.

All percentages and ratios used herein are by weight and all measurements are at room temperature, unless otherwise indicated. As used herein, "ml" means milliliter, "mm" means millimeter, and "nm" means nanometer.

BRIEF DESCRIPTION OF THE DRAWING

The FIGURE is an idealized rheogram which is useful for graphically showing a number of terms and concepts used in the present invention. The FIGURE is a plot of the Log of the applied shear stress to the Log of the viscosity. A represents the zero shear viscosity. B represents the yield stress, and C represents high shear viscosity.

DETAILED DESCRIPTION OF THE INVENTION

The FIGURE plots the Log of the applied shear stress to the Log of the viscosity. The FIGURE is a representative rheogram resulting from the testing of a viscous shear thinning liquid material in a controlled-stress rheometer. In the stress ramp test, which can be conducted at room temperature or body temperature, depending on the objective of the experiment, initially very low shear stress is applied to the sample, and gradually but continually the shear stress is increased, all the while determining the shear rate resulting in the sample. The FIGURE is useful for defining terms related to the viscosity and flow properties of liquid materials, particularly the shear thinning liquids claimed herein. The term "shear thinning" as used herein refers to a liquid having a higher viscosity when the applied shear is very low. At higher shear forces a shear thinning liquid has a lower viscosity. This characteristic low viscosity of a shear thinning composition under high shear stress is termed the "high shear viscosity" C. As the structure in the liquid is largely undisturbed by the initial low shear stress applied in the test, the composition's viscosity does not change to a large degree. As shear stress is increased, however, there will be a disproportionate increase in shear rate (flow) as the internal structure in the fluid breaks down, and correspondingly, viscosity decreases. The stress applied to the fluid at which rapid flow just begins to occur is termed the "yield stress" (or "yield value") B.

Zero shear viscosity A is a measure of the internal structure in the liquid formulation and is the viscosity when stress below the yield stress is applied. Zero shear viscosity may be accurately determined by the method of creep compliance using a sensitive, controlled stress rheometer. This method is described in the book "A Practical Approach to Rheology and Rheometry", by Gebhard Schramm, 1994 p.107, which is incorporated herein by reference in its entirety. An about 0.9 ml volume sample of the liquid is placed onto the plate of the rheometer (Haake RS150), and a 35 mm, 4 degree angle cone measurement sensor lowered to the measurement position. An equilibration shearing of about 20 per second is applied for about 10 to 20 seconds; then no stress is applied for 2 minutes. At the end of the 2 minutes, an instantaneous stress is applied and held constant for 5 minutes. This creep stress must be below the yield stress. A graph of the strain induced in the sample on the y axis against the time that the creep stress is applied on the x axis is generated. This graph will display an instantaneous large increase in strain at the beginning of the test, and after some period of curvature the graph will show that the strain increases proportionally in a straight line with time. The calculated slope of this strain-time line is divided into the applied creep stress to give a viscosity. As long as the creep stress is below the yield stress of the liquid, then the viscosity determined in this manner is the zero shear viscosity A. Colloidal suspensions of the present invention should have high zero shear viscosity. Zero shear viscosity of the compositions herein should be greater than about 2,000 pascal seconds, preferably greater than about 7,500 pascal seconds, more preferably greater than about 25,000 pascal seconds. Other terms useful herein are defined below. Additionally, terms used in the art, as well as general concepts, are further described in "The Language of Colloid and Interface Science" by Laurier L. Schramm, American Chemical Society, 1993, which is incorporated herein by reference in its entirety.

The term "shear" as used herein is the rate of deformation of a fluid when subjected to a mechanical shearing stress. In simple fluid shear, successive layers of fluid move relative to each other such that the displacement of any one layer is proportional to its distance from a reference layer. The relative displacement of any two layers divided by their distance of separation from each other is termed the "shear" or the "shear strain". The rate of change with time of the shear is termed the "shear rate".

A certain applied force is needed to produce deformation in a fluid. For a plane area around some point in the fluid and in the limit of decreasing area the component of deforming forces per unit area that acts parallel to the plane is the "shear stress".

The "viscosity" of a viscous material, also called viscosity index, is defined as the ratio of the shear stress applied into the material, divided by the rate of shear which results. Materials of a higher viscosity have a higher resistance to flow, or to forces which can induce flow, than a lower viscosity material. All viscosities listed herein are at a shear rate of about 50 per second unless otherwise indicated. All of the rheologic characteristics given herein can be measured in a controlled stress rotational viscometer capable of some operation in a controlled rate mode, for Example Haake RS 150 by Haake GmbH, Karlsruhe, Germany; Carrimed CSL 500 Controlled Stress Rheometer by TA Instruments, New Castle, Del.; and Rheometric SR5, by Rheometric Scientific, Piscataway, N.J.

The present invention relates to mucoadhesive formulations comprising colloidal suspensions which form a coating matrix on the epithelium of the alimentary canal and/or the gastrointestinal tract. The term "colloidal" as used herein refers to finely divided solid material in which the particles of $TiO_2$, $SiO_2$, and/or clay (dispersed in another, liquid phase) have a particle size of generally less than 10 microns, or the particles have at least one dimension between about 1 and about 1000 nm. The particle size of the solid particles of the present invention are of colloidal dimension (about 1 nm to about 10 microns), preferably about 1,000 nm's or smaller. The small particle size increases surface area for improved adsorption or bridging of the particle to mucin.

The term "colloidal suspension" as used herein refers to a system in which essentially solid colloidal particles are dispersed in a continuous phase of different composition or state, for example water. The colloidal suspensions of the present invention form a coating matrix on the mucosal epithelium of the alimentary canal and/or gastrointestinal tract.

The term "mucoadhesive" or "bioadhesive" as used herein refers to the phenomenon where a natural or synthetic substance applied to a mucosal epithelium, adheres, usually creating a new interface, to the mucus layer. (*CRC Critical Reviews in Ther Drug Carrier*, Vol. 5 issue 1 (1988) pp. 21.) Generally, mucoadhesion can be achieved via physical or chemical processes or both. This mechanism is described in *J. Controlled Release,* Vol. 2 (1982) pp. 257 and *J. Controlled Release,* Vol. 18 (1992) pp. 249. The above references are incorporated by reference herein in their entirety.

The term "mucoretentive" (or "retentive") as used herein refers to a degree of resistance to the normal physiological propulsive mechanism involving both longitudinal and circular muscle fiber contraction, which transports substances through the gastrointestinal tract, i.e. resistance to peristalsis. Also, "mucoretentive" refers to a composition's degree of resistance to washing and dissolving forces of fluids in the gastro intestinal tract. The inventor has devised and employed a test which measures the tendency of a liquid formulation to coat onto tissues of the alimentary canal and/or gastrointestinal tissue and to resist the shear and rinsing forces of gastrointestinal fluid. This test was based on a method used to evaluate the ability of gastrointestinal therapeutic formulations to bind and be retained on esophageal mucosa, L. R. Fitzpatrick et al, "A comparison of sucralfate and bismuth subsalicylate formulations in rabbit esophageal models", *Gastroenetrology* Vol. 108, page A94. This reference is incorporated herein by reference in its entirety. In this method a freshly collected esophagus of a rabbit or a rat is cut into sections of about 2 cm in length. The tissue is everted onto a glass rod so that the mucosal surface is facing out. This mucosal surface can then be dipped into the formulation. Formulations with preferred rheology properties will tend to spread onto the mucosa and then form a coherent coating layer. The resistance to mechanical force and washing can be determined by vertically immersing the coated tissue into gastrointestinal fluid again and again by reciprocation. The amount of formulation which remains coated onto the tissue at the end of 30 rinses in gastrointestinal fluid has been determined to be a useful number for determining whether a formulation has mucoretentive properties. (Gastrointestinal fluid includes saliva, gastric juice, intestinal fluid, mixtures thereof, and Simulated Gastric Fluid TS USP disclosed in US Pharmacopeia 23, 1995, US Pharmacopeial Convention, Rockville, Md. p. 2053.) This may be quantified by a specific chemical analytical technique for a component of the formulation, or by incorporation of an easily measured, non-diffusing colloidal marker material into the formulation prior to testing. Mucoretentive compositions of the present invention have, after 30 rinses in simulated saliva, at least about 80% of the initial amount still adhered to the tissue, preferably at least about 85%, more preferably at least about 90%. Simulated saliva used for this test is adapted from Fusayama, T., Katayori, S., Nomoto, S., 1963. "Corrosion of gold and amalgam placed in contact with each other". *J. Dent. Res.*42, 1183–1197 and contains on a mg/ml basis: KCl 0.4; NaCl 0.4; $Na_2SO_4$ 0.013; $MgCl_2$ 0.018; $KH_2PO_4$ 4.2; $KH_2PO_4$ 3.2, KOH 0.19, and bovine submaxillary mucin 4.0.

Mucoretentive compositions of the present invention, for use in the treatment of gastrointestinal disorders, have, after 30 rinses in similated gastric fluid, at least about 80% of the initial amount still adhered to the tissue, preferably at least about 85%, more preferably at least about 90%.

The term "alimentary canal" as used herein refers to that part of the gastrointestinal tract formed by the nasal cavity, oral cavity, esophagus, stomach, and the small intestine.

The term "glycoprotein" as used herein refers to a class of conjugated proteins comprising a protein compound with a carbohydrate group. Glycoproteins yield, in decomposition, a product frequently capable of reducing alkaline solutions of cupric oxide. Glycoproteins include mucins, mucoids, and the chondroproteins. The term "mucin" as used herein includes that which is contained in the saliva, gastrointestinal fluid and/or associated with the surface of the tissue of the alimentary canal and gastrointestinal tract. Mucin is produced within the body and provides lubrication and protection to the mucosal surfaces. It consists of a protein backbone, onto which are attached many polysaccharide chains. In the dry state, the mucin material is 70 to 80 percent by weight, carbohydrate. Mucin, with its high molecular weight, forms threadlike chains as much as 4–6 microns long, and may be effective in bridging of a colloidal suspension of particles which adsorbs it. (Neutra M. R. and Forstner F. J. "Gastointestinal mucus:Synthesis, secretion, and function." *Physiology of the Gastrointestinal Tract,* 1987, pp. 975–1009.)

In order to provide suspensions with acceptable aesthetics, it is desirable for the suspensions to thin when they are shaken and/or poured into a spoon, cup, or other dosing apparatus. Such shaking and pouring subjects the suspensions to a shear rate of from about 10 to about 1,000 per second. Furthermore, when swallowed, a liquid is subject to a shear rate of from about 10 to about 100 per second. It is also critical that the suspensions significantly thin when swallowed in order to achieve adequate spreading and coating of the alimentary canal and gastrointestinal tract.

Specifially, when subject to constant shearing rate of about 100 per second, the present liquid compositions have a viscosity of less than about 1.5 pascal seconds, preferably less than about 0.75 pascal seconds, more preferably less than about 0.5 pascal seconds.

The solid particles of the present invention must be selected and formulated so that the contacting and mixing of the formulation of the present invention (hereinafter "the formulation") to a mucosal surface of the alimentary canal triggers the conversion of the formulation to a more viscous gel-like mixture. In other words, after the formulation mixes with gastrointestinal fluid, the viscosity of the formulation is greater than the viscosity of either the formulation prior to mixing, or the gastrointestinal lining fluid mixture alone.

The value of a formulation's triggered viscosity ratio ("T") is useful in determining the degree to which a composition exhibits the above described gelling characteristic. The formula and procedure for determining the triggered viscosity ratio is set forth below.

It is desirable for the compositions of the present invention to exhibit a triggered viscosity ratio of at least about 1.2, more preferably at least about 1.4, and most preferably at least about 1.5 where the triggered viscosity is defined by the following formula:

$$T = \frac{\eta_g}{\eta_f}$$

where $\eta_g$=viscosity of the gel and where $\eta_f$=viscosity of the formulation of the present invention As used herein, the term "gel" describes the substance resulting from the combination of mucin/saliva mixture and the formulation of the present invention. For determining the triggered viscosity ratio herein, the mucin saliva mixture contains on a mg/ml basis: KCl 3.32; NaCl 3.32; $Na_2SO_4$ 0.108; $MgCl_2$ 0.150; $KH_2PO_4$ 34.86; $KH_2PO_4$ 26.56, KOH 1.57, and bovine submaxillary mucin 83. A commercial supply of mucin is available from Sigma Chemical Co., St. Louis, Mo., as bovine submaxillary mucin type I, catalog # M4503.

The triggered viscosity ratio of a formulation can be determined by the following method. First, the viscosity of the formulation ($\eta_f$) is determined in a rheometer using a shear rate of 50 per second. For the determination of $\eta_f$, 0.9 ml of the formulation is placed onto the plate of a Haake RS150 rheometer. The temperature is controlled in the range of typical room temperature, about 23° C. A cover is used on the measuring system to prevent evaporation of water from the sample during the test. A 35 mm diameter, 4 degree angle cone measuring system is lowered onto the sample, and an equilibration shearing of approximately 20 per second is applied for 20 seconds. After a rest period wherein no stress is applied for 2 minutes, a constant shearing rate of 50 per second is applied for 65 seconds. The viscosity $\eta_f$ is read from the instrument at the 60 second time point.

For the determination of $\eta_g$, 0.5 ml of the mucin/saliva mixture, described above, is combined with 4.5 ml of the formulation and the two are gently mixed together for 5 minutes. The mixture is then loaded onto the plate of the same rheometer used for the measurement of $\eta_f$, except that the temperature is controlled at the normal body temperature of a human, 37° C. An identical rheometer measurement program is used as for determination of $\eta_f$. The triggered viscosity factor is calculated from $\eta_f$ and $\eta_g$ as described by the formula above.

The mucoadhesive dispersion of the present invention has various benefits: protection of the mucosa from acid, pepsin, bile, food or drink known to induce irritations such as heartburn or dyspepsia; exogenous or endogenous irritants which induce cough or sore throat or which cause nasal congestion; promote the healing of injured mucosa due to ulcers, gastric content reflux, etc.; sustained retention of actives on the mucosa; sustained release of actives on the mucosa or throughout the alimentary canal and/or gastrointestinal tract; etc. The compositions of the present invention provide coating on both inflamed and/or damaged tissue as well as normal mucosal tissue.

Preferably, the compositions of the present invention comprise only low levels of bioadhesive polymers, especially high molecular weight polymers, preferably less than about 1%, more preferably less than about 0.5%, even more preferably are essentially free of bioadhesive polymers, especially high molecular weight polymers; for example, those having a molecular weight of at least about 2,000 such as those disclosed in U.S. Pat. No. 5,458,879, Singh et al., issued Oct. 17, 1995, which is incorporated herein by reference in its entirety. Preferably, if the compositions of the present invention comprise a polymer, the ratio of colloidal particles (clay, silica, and/or titanium dioxide) to polymer is at least 10:1, preferably at least 20:1; more preferably, at least about 35:1 to 45:1.

Sedimentation Volume Ratio

Another essential feature of the compositions of the present invention is that the compositions have a sedimentation volume ratio of greater than about 0.90, preferably greater than about 0.95, more preferably greater than about 0.98, and even more preferably about 1, (after about 48 hours). Sedimentation volume ratio is determined by carefully filling a sample of the formulation into a clear glass graduated cylinder, capping the cylinder to prevent any evaporation, and allowing the formulation to remain undisturbed and free from significant vibration. After at least 48 hours, total occupied volume in the cylinder ($V_o$) and the ultimate volume ($V_u$) of any sediment which may have formed by settling of components of the suspension below the total volume is determined. This procedure is explained in "Coarse Dispersions", Chapter 18 in *Physical Pharmacy*, A. Martin, Lea and Febiger, Malvern, Pa., 1993, page 480, which is incorporated herein by reference. The sedimentation volume ratio is the ratio of the ultimate volume to the occupied volume ($V_u/V_o$).

More preferably the colloidal particles of the composition of the present invention have a concentration greater than that which is required to have a sedimentation volume ratio of 1.0.

Particulate Component

The compositions of the present invention comprise a safe and effective amount of a particulate component which provides the mucoadhesive benefit. The particulate component comprises colloidal particles selected from the group consisting of silica, titanium dioxide, clay, and mixtures thereof.

Silicon Dioxide (Silica)

The silicon dioxide is present at a level of from about 2% to about 50% by weight of the composition, preferably from about 3% to about 20%, more preferably from about 4% to about 9% by weight. Any of the available forms are acceptable for use in the present invention such as fumed silicon dioxide, precipitated silicon dioxide, colloidal silicon dioxide, coacervated or gels. Fumed silicon dioxide is especially effective at about 5% to about 20% by weight. These silica particles may be chemically surface modified, for example with methyl siloxane, to enhance the tissue barrier properties of the coating to hydrophilic substances.

Small particle size silicon dioxide is preferred, i.e. silicon dioxide having a mean particle size of less than about 1 micron.

Titanium Dioxide

The titanium dioxide is present at a level of from about 2% to about 50% by weight of the composition, preferably from about 3% to about 20%, more preferably from about 4% to about 9% by weight. Any of the available pharmaceutical grade forms of titanium dioxide are acceptable for use in the present invention as long as such form achieves the mucin interaction (T values) described above and efficiently achieves acceptable sedimentation volume ratio as specified herein. Such forms include rutile, anatase crystalline form, amorphous form, and any other form which is acceptable for the purposes of the present invention. These titanium dioxide particles can be chemically surface modified, for example with alumina, silica, or other stabilizing agent, to enhance the tissue barrier properties of the coating to hydrophilic substances.

The two major processes used in manufacturing titanium dioxide are sulfate and chloride. The processes are usually followed by modification of particle surfaces with treatments and coatings. Certain additives are used for modifying the titanium dioxide which affect the surface properties, for example zinc salts that form zinc titanate at the crystal surfaces, alumina, silica, and titania coatings in aqueous dispersions. In addition titanium dioxide can be further modified by organic surface treatments. Organic surface treatments include surface active agents, saturated and unsaturated fatty acid, oleic acid, dehydrated castor oil acid, and derivatives of these compounds, and mixtures thereof. Further details of surface properties of titanium dioxide are found in H. S. Ritter, "Surface Properties of Titanium Dioxide Pigments", *Pigment Handbook*, Chem. Div. PPG Ind., (1973), Vol. 3, pp. 169–184.

Small particle size titanium dioxide is preferred, i.e. titanium dioxide having a mean particle size of less than about 1 micron. More preferably, compositions comprise uncoated titanium dioxide having a mean particle size of from about 20 nm to about 400 nm, even more preferably about 50 nm. Titanium dioxide and silica products include those available from Warner Jenkinson, S. Plainfield, N.J.; Degussa, Ridgefield Park, N.J.; Cabot Corp., Tuscola, Ill.

Clays

The clay is present at a level of from about 2% to about 50 % by weight of the composition, preferably from about 3.5% to about 20%, more preferably from about 4.0% to about 10% by weight. Clays are composed of fine particles of clay minerals which are layer-type hydrous (containing structural hydroxyl groups) silicates of aluminum, magnesium, potassium, iron, and other less abundant elements, particularly alkalis and alkaline earth metals. Preferred are silicates of aluminum, magnesium and iron. More preferred are silicates of aluminum. Preferred is magnesium aluminum silicate (or aluminum magnesium silicate), occurring naturally in such smectite minerals as colerainite, saponite, and sapphirine. Refined magnesium aluminum silicates useful herein are readily available as Veegum, manufactured by R. T. Vanderbilt Company, Inc.

Clay may also contain varying amounts of non-clay minerals such as quartz, calcite, feldspar, and pyrite. Preferred clays useful herein are water swellable clays.

The term "clay" as used herein includes but is not limited to kaolin minerals such as kaolinite, china clay, dickite, nacrite, halloysite; serpentine minerals such as lizardite, halloysite, chrysotile, antigorite, carlosturanite, amestite, cronstedite, chamosite, berthierine, garierite; talc; pyrophyllite; ferripyrophyllite; smectites such as montmorillonites, beidellite, nontronite, hectorite, saponite, sauconite, medmontite, pimelite, bentonite; illite minerals such as ledikete, bravaisite, degraded mica, hydromica, hydromuscovite, hydrous illite, hydrous mica, K-mica, micaceous clay, and sericite; mica such as pegmatite, muscovite, and phlogopite; brittle mica such as margarite, and clintonite; glauconite; celadonite; chlorite and vermiculite such as pennine, clinochlore, chamosite, nimite, baileychlore, donbassite, cookite, sudoite, franklinfurnaceite; palygorskite and sepiolite minerals such as attapulgite; allophane and imogolite; mixed layer clay minerals such as talc-chlorite; and mixtures thereof.

Preferred clays are selected from the group consisting of kaolin minerals, smectites, mica, and mixtures thereof. More preferred are clays selected from the group consisting of laponite, bentonite, hectorite, saponite, montmorillonites, and mixtures thereof.

Any of the available forms are acceptable for use in the present invention such as colloidal clays, for example magnesium aluminosilicate, magnesium bentonite, attapulgite, sodium bentonite magma, etc.

Clays which are useful in the present invention include both mined, naturally occurring clays as well as synthetic clays. The clays must be pharmaceutically-acceptable. A more detailed description of the clays and clay minerals useful herein can be found in the following three references, each of which is incorporated by reference in its entirety: Kirk-Othmer, *Encyclopedia of Chemical Technology*, Fourth Edition, Vol. 6, pages 381–423; Dell, D. J., "Smectite Clays in Personal Care Products", *Cosmetics & Toiletries*, Vol. 108, May 1993, pages 79–85; and Theng B. K. G., "Formation and Properties of Clay-Polymer Complexes", *Developments in Soil Science*, Vol. 9. Clays include products available from Southern Clay Products, Gonzalez, Tex.; Generichem, Totowa, N.J.; R. T. Vanderbilt, Norwalk, Conn.; Smeotite, Inc., Casper, N.Y.

The Active Agent

The compositions of the present invention also comprise a safe and effective amount of at least one pharmacologically active agent selected from the group consisting of: (a) analgesics, (b) decongestants, (c) expectorants, (d) antitussives, (e) antihistamines, (f) bronchodilators, (g) topical anesthetics, (h) sensory agents, (i) oral care agents, (j) miscellaneous respiratory agents, (k) gastrointestinal agents, and mixtures thereof. The level of pharmacologically active agent is from about 0.01% to about 50%, preferably from about 0.1% to about 35%, by weight of the composition, unless otherwise indicated. The active agent can be water soluble, slightly water soluble, or insoluble in water and have particle sizes generally of at least 1 micron.

Analgesics

The analgesics useful for this invention include any narcotic and non-narcotic analgesics, such as menthol, acetaminophen, NSAIDs, salicylates including aspirin (acetylsalicylic acid), salsalate, sodium salicylate, diflunisal, etc. and mixtures thereof, indomethacin and optically active isomers or racemates or active metabolites of NSAIDs (NSAIDs include propionic acid derivatives, acetic acid derivatives, fenamic acid derivatives, biphenylcarboxylic acid derivatives and oxicams) including fenoprofen, flurbiprofen, ibuprofen, ketoprofen, naproxen, oxaprozin, etodolac, indomethacin, ketorolac, nabumetone, sulindac, tolmetin, meclofenamate, mefenamic acid, piroxicam, bromfenac, carprofen, tiaprofenic acid, cicloprofen, diclofenac, benzydomine, their pharmaceutically acceptable salts and mixtures thereof. All of these, as well as acceptable dosage ranges, are described in the following: U.S. Pat. No. 4,749,720 to Sunshine et al. issued Jun. 7, 1988; U.S. Pat. No. 4,749,721 to Sunshine et al. issued Jun. 7, 1988; U.S. Pat. No. 4,749,722 to Sunshine et al. issued Jun. 7, 1988; U.S. Pat. No. 4,749,723 to Sunshine et al. issued Jun. 7, 1988; U.S. Pat. No. 4,749,711 to Sunshine et al. issued Jun. 7, 1988, U.S. Pat. No. 4,749,697 to Sunshine et al. issued Jun. 7, 1988, U.S. Pat. No. 4,783,465 to Sunshine et al., issued Nov. 8, 1988, U.S. Pat. No. 4,619,934 to Sunshine et al., issued Oct. 28, 1986, U.S. Pat. No. 4,840,962 to Sunshine et al. issued Jun. 20, 1989; U.S. Pat. No. 4,906,625 to Sunshine et al. issued Mar. 6, 1990; U.S. Pat. No. 5,025,019 to Sunshine et al. issued Jun. 18, 1991; U.S. Pat. No. 4,552,899 to Sunshine et al. issued Nov. 12, 1985, *Facts and Comparisons*, 1998, p. 242–260, all of which are incorporated by reference herein, in their entirety.

Decongestants, Expectorants, Antitussives

The decongestants prepared for use in the compositions of the present invention include pseudoephedrine, phenylpropanolamine, phenylephrine, epinephrine, ephedrine, their pharmaceutically acceptable salts, and mixtures thereof.

The expectorants (also known as mucolytic agents) preferred for use in the present invention include guaifenesin, iodinated glycerol, glyceryl guaiacolate, terpin hydrate, ammonium chloride, N-acetylcysteine and bromhexine, ambroxol, iodide, their pharmaceutically acceptable salts, and mixtures thereof.

The antitussives preferred for use in the present invention include those such as menthol (can also be used as an analgesic), dextromethorphan, chlophedianol, carbetapentane, caramiphen, noscapine, diphenhydramine, codeine, hydrocodone, hydromorphone, fominoben, benzonatate, their pharmaceutically-acceptable salts, and mixtures thereof.

All of these components, as well as their acceptable dosage ranges are described in the following: U.S. Patents to Sunshine et al. listed above under analgesics; U.S. Pat. No. 4,619,934 to Sunshine et al., issued Oct. 28, 1986, *Facts and Comparisons*, 1998, p. 173–228, which are incorporated by reference herein in their entirety.

Antihistamines

Examples of antihistamine agents preferred for use in the present invention include both sedating and non-sedating antihistamines, such as diphenhydramine, clemastine, chlorpheniramine, dexchlorpheniramine, brompheniramine, dexchlorpheniramine, dexbrompheniramine, triprolidine, doxylamine, tripelennamine, cyproheptadine, carbinoaxime, doxylamine, bromdiphenhydramine, hydroxyzine, pyrilamine, promethazine, acrivastine, AHR-11325, phenindamine, astemizole, azatadine, azelastine, cetirizine, ebastine, fexofenadine, ketotifen, lodoxine, loratidine, descarboethoxyloratadine, levocabastine, mequitazine, oxatomide, setastine, tazifyline, temelastine, terfenadine, tripelennamine, terfenadine carboxylate, phenyltoloxamine, pheniramine, pharmaceutically acceptable salts thereof, pharmaceutically active metabolites thereof, optically active isomers or racemates, and mixtures thereof. All of these antihistamines, as well as their acceptable dosage ranges, are described in: U.S. Patents to Sunshine et al. listed above under analgesics; *Facts and Comparisons,* 1998, p. 188–195, which is incorporated by reference herein in its entirety.

Bronchodilators

Also useful are bronchodilators such as terbutaline sulfate, isoetharine, aminophylline, oxtriphylline, dyphylline, ethylnorepinephrine, isoproterenol, epinephrine, isoprenaline, metaproterenol, bitoterol, theophylline, albuterol, isoproterenol and phenylephrine bitartrate, bitolterol, ephedrine sulfate, pirbuterol acetate, pharmaceutically acceptable salts thereof, and mixtures thereof. All of these bronchodilators, as well as their acceptable dosage ranges, are described in *Facts and Comparisons,* 1998, p. 173b–179e, which is incorporated by reference herein in its entirety.

Topical Anesthetics

Topical anesthetics include lidocaine, dibucaine, dyclonine, benzocaine, butamben, tetracaine, pramoxine, their pharmaceutically-acceptable salts, and mixtures thereof. All of these agents, as well as their acceptable dosage ranges, are described in *Facts and Comparisons,* 1998, p. 601–607, which is incorporated by reference herein in its entirety.

Sensory Agents

Also useful herein are sensory agents selected from the group consisting of coolants, salivating agents, warming agents. Preferably these agents are present in the compositions at a level of from about 0.001% to about 10%, preferably from about 0.1% to about 1%, by weight of the composition.

Suitable cooling agents include carboxamides, menthols, thymol, camphor, capsicum, phenol, eucalyptus oil, benzyl alcohol, salicyl alcohol, ethanol, clove bud oil, and hexylresorcinol, ketals, diols, and mixtures thereof. Preferred coolants are the paramenthan carboxyamide agents such as N-ethyl-p-menthan-3-carboxamide (WS-3 supplied by Sterling Organics), taught by U.S. Pat. No. 4,136,163, issued Jan. 23, 1979, to Watson et al., which is incorporated herein by reference in its entirety. Another preferred paramenthan carboxyamide agent is N,2,3-trimethyl-2-isopropylbutanamide, known as "WS-23", and mixtures of WS-3 and WS-23.

Additional preferred coolants are selected from the group consisting of menthol, 3-1-menthoxypropane-1,2-diol, known as TK-10 supplied by Takasago Perfumery Co., Ltd., Tokyo, Japan, menthone glycerol acetal known as MGA, manufactured by Haarmann and Reimer, menthyl lactate known as Frescolat® manufactured by Haarmann and Reimer, and mixtures thereof.

Additional cooling agents include cyclic sulphones and sulphoxides and others, all of which are described in U.S. Pat. No. 4,032,661, issued Jun. 28, 1977, to Rowsell et al., which is herein incorporated by reference.

The terms "menthol" and "menthyl" as used herein include dextro- and levorototory isomers of these compounds and racemic mixtures thereof.

TK-10 is described in detail in U.S. Pat. No. 4,459,425, issued Jul. 10, 1984 to Amano et al. and incorporated herein by reference.

Salivating agents of the present invention include Jambu® manufactured by Takasago Perfumery Co., Ltd., Tokyo, Japan.

Warming agents include capsicum and nicotinate esters, such as benzyl nicotinate.

Miscellaneous Respiratory Agents

Also useful herein are miscellaneous respiratory agents selected from the group consisting of leukotriene receptor antagonists such as zafirlukast, zileuton; nasal inhalant products such as corticosteroids, other steroids, beclomethasone, flunisolide, triamcinolone; mucolytics such as acetylcysteine; anticholinergics such as ipratropium bromide; cromolyn sodium, nedocromil sodium; lung surfactants; and mixtures thereof.

Preferably these agents are present in the compositions at a level of from about 0.001% to about 10%, preferably from about 0.1% to about 5%, by weight of the composition.

Oral Care Agents

The active agent of the present invention can also comprise those agents useful for the treatment of disorders of the oral cavity such as plaque, gingivitis, periodontal disease, oral malodor, and caries. These agents include antimicrobials, fluoride, antiinflammatory agents, bisphosphonates, anticalculus agents such as pyrophosphates, H-2 receptor antagonists, and mixtures thereof.

Antimicrobials

Antimicrobial agents can also be present in present compositions. Such agents may include, but are not limited to, triclosan, 5-chloro-2-(2,4-dichlorophenoxy)-phenol, as described in *The Merck Index,* 11th ed. (1989), pp. 1529 (entry no. 9573) in U.S. Pat. No. 3,506,720, and in European Patent Application No. 0,251,591 of Beecham Group, PLC, published Jan. 7, 1988; chlorhexidine (Merck Index, no. 2090), alexidine (Merck Index, no. 222; hexetidine (Merck Index, no. 4624); sanguinarine (Merck Index, no. 8320); benzalkonium chloride (Merck Index, no. 1066); salicylanilide (Merck Index, no. 8299); domiphen bromide (Merck Index, no. 3411); cetylpyridinium chloride (CPC) (Merck Index, no. 2024; tetradecylpyridinium chloride (TPC); N-tetradecyl-4-ethylpyridinium chloride (TDEPC); octenidine; delmopinol, octapinol, and other piperidino derivatives; nicin preparations; zinc/stannous ion agents; antibiotics such as augmentin, amoxicillin, tetracycline, doxycycline, minocycline, and metronidazole; nystatin, tannic acid (forms protective film over cold sores, fever blisters, and canker sores), clotrimazole, carbamide peroxide, amlexanox (indicated for treatment of aphthous ulcers); and analogs and salts of the above antimicrobial antiplaque agents. The antimicrobial agents generally comprise from about 0.1% to about 5% by weight of the compositions of the present invention.

Antiinflammatory Agents

Antiinflammatory agents may also be present as the active agent in the compositions of the present invention. These agents are disclosed above under the analgesic section. The antiinflammatory agents generally comprise from about 0.001% to about 5% by weight of the compositions of the present invention.

Fluoride tons

The present invention may also incorporate free fluoride ions. Preferred free fluoride ions can be provided by sodium fluoride, stannous fluoride, indium fluoride, and sodium monofluorophosphate. Sodium fluoride is the most preferred free fluoride ion. Norris et al., U.S. Pat. No. 2,946,725, issued Jul. 26, 1960, and Widder et al., U.S. Pat. No. 3,678,154 issued Jul. 18, 1972, disclose such salts as well as others. These patents are incorporated herein by reference in their entirety.

The present composition may contain from about 50 ppm to about 3500 ppm, and preferably from about 500 ppm to about 3000 ppm of free fluoride ions.

Anticalculus Agents

The present invention may also include an anticalculus agent, preferably a pyrophosphate ion source which is from a pyrophosphate salt. The pyrophosphate salts useful in the present compositions include the dialkali metal pyrophosphate salts, tetraalkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, preferably from about 1.5% to about 10%, and most preferably from about 2% to about 6%. Free pyrophosphate ions may be present in a variety of protonated states depending on a the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is the preferred pyrophosphate salt in these compositions. Tetrasodium pyrophosphate may be the anhydrous salt form or the decahydrate form, or any other species stable in solid form in the present compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, and is generally from about 1.5% to about 15%, preferably from about 2% to about 10%, and most preferably from about 3% to about 8%, by weight of the composition.

Compositions may also comprise a mixture of dissolved and undissolved pyrophosphate salts. Any of the above mentioned pyrophosphate salts may be used.

The pyrophosphate salts are described in more detail in Kirk & Othmer, *Encyclopedia of Chemical Technology*, Third Edition, Volume 17, Wiley-Interscience Publishers (1982), incorporated herein by reference in its entirety, including all references incorporated into Kirk & Othmer.

Optional agents to be used in place of or in combination with the pyrophosphate salt include polyamino propoane sulfonic acid (AMPS), zinc citrate trihydrate, polyphosphates, diphosphonates (e.g., EHDP; AHP), polypeptides (such as polyaspartic and polyglutamic acids), and mixtures thereof.

H-2 Receptor Antagonist

The active agent of the present invention can also be a selective H-2 antagonists including compounds disclosed in U.S. Pat. No. 5,294,433, Singer et al., issued Mar. 15, 1994, which is herein incorporated by reference in its entirety.

Gastrointestinal Agents

Examples of gastrointestinal agents preferred for use in the present invention include anticholinergics, including: atropine, clidinium and dicyclomine; antacids, including aluminum hydroxide, basic bismuth salts such as bismuth subsalicylate, bismuth ranitidine citrate, bismuth subcitrate, bismuth subnitrate, aluminum or bismuth salts of polysulfated saccharides such as aluminum sucrose octasulfate or bismuth sucrose octasulfate, simethicone, calcium carbonate and magaldrate (other examples of antacids can be found in 21CFR 331.11 which is incorporated herein by reference); $H_2$-receptor antagonists, including cimetidine, famotidine, nizatidine and ranitidine; laxatives, including: bisacodyl, picosulfate, and casanthrol (other examples of laxatives can be found in the Federal Registry, Vol. 50, No. 10, Jan. 15, 1985, pp. 2152–58, which is incorporated herein by reference); gastroprotectants, including sucralfate and sucralfate humid gel; gastrokinetic and prokinetic agents including cisapride, metoclopramide and eisaprode; proton pump inhibitors including omeprazole, lanzoprazole, and antidiarrheals including: diphenoxylate and loperamide; agents which are bacteriostatic or bactericidal to the ulcer-inducing organism *Heliobacter pylori* such as amoxicillin, metronidazole, erythromycin, or nitrofurantoin and others agents for treating *H. pylori* disclosed in U.S. Pat. No. 5,256,684, Marshall, issued Oct. 26, 1993, The Procter & Gamble Company which is incorporated herein by reference in its entirety; polyanionic materials useful for the treatment of ulcers and other gastrointestinal disorders including amylopectin, carragemum, sulfated dextrins, inositol hexaphosphate, or other similar agents.

The term "pharmaceutically acceptable salts" refers to salts prepared from pharmaceutically acceptable nontoxic bases including inorganic bases and organic bases. Salts derived from nonorganic bases include sodium, potassium, lithium, ammonia, calcium, magnesium, ferrous, zinc, manganous, aluminum, ferric, manganic salts and the like. Salts derived from pharmaceutically acceptable organic nontoxic bases include salts of primary, secondary, tertiary and quaternary amines, substituted amines including naturally occurring substituted amines, cyclic amines and basic ion exchange resins, such as triethylamine, tripropylamine, 2-dimethylaminoethanol, 2-diethylaminoethanol, lysine, arginine, histidine, caffeine, procaine, N-ethylpiperidine, hydrabamine, choline, betaine, ethylenediamine, glucosamine, methylglycamine, theobromine, purines, piperazine, piperidine, polyamine resins and the like.

Also, extracts of plants or other natural substances known to be effective in any gastrointestinal disorder can be delivered from the mucoadhesive composition of the present invention.

Pharmaceutically-Acceptable Excipients

The liquid phase of the colloidal suspensions of the present invention is generally water. These compositions comprise from about 5% to about 98%, preferably from about 70% to about 95%, by weight of the composition, of water.

Optionally, these aqueous compositions also contain suitable amounts of preservatives, buffers, emulsifying agents, suspending agents, diluents, natural or artificial sweeteners, taste-masking agents, coloring agents, and flavoring agents, to provide a palatable and/or pleasant looking final product. Also, compositions may also comprise antioxidants, for example, butylated hydroxy anisole or butylated hydroxy toluene, and preservatives, for example, methyl or propyl paraben or sodium benzoate, to prolong and enhance shelf life.

To provide consistent dispersion of the solid particles thereby improving stablity, especially for formulations comprising silica, the compositions of the present invention may optionally contain from about 0.005% to about 3%, preferably from about 0.01% to about 1.5% of a substituted or unsubstituted, short chain, e.g. $C_1$ to $C_6$, alkyl or aryl carboxylic acid including citric acid, tartaric acid, butyric acid, acetic, malic, maleic, succinic acid, mixtures thereof and salts thereof. Especially preferred is sodium citrate.

Specific examples of pharmaceutically acceptable carriers and excipients that may be used to formulate oral dosage forms, are described in U.S. Patents to Sunshine et al. listed above under analgesics section.

Pharmaceutically-Acceptable Aqueous Nasal Excipients

For intranasal compositions, the compositions of the present invention comprise a pharmaceutically-acceptable intranasal carrier. Preferred for use herein are aqueous saline solution carriers. These solutions which generally contain sodium chloride as the salt are fully described in *Remington's Pharmaceutical Sciences*, 19$^{th}$ edition (1995) p. 1502, which is herein incorporated by reference. The salt is present in the solution at a level of about 0.01% to about 2%, preferably from about 0.5% to about 1.0% by weight of solution. Suitable nontoxic pharmaceutically-acceptable nasal carriers are known to those skilled in the art. Obviously, the choice of a suitable carrier will depend on the exact nature of the particular nasal dosage form required, e.g., whether the active agent is to be formulated into a nasal solution (for use as drops or as a spray), a nasal suspension, a nasal ointment, a nasal gel or another nasal form. Preferred nasal dosage forms are solutions, suspensions and gels, which normally contain sodium chloride in a major amount of water (preferably purified water). Minor amounts of other ingredients such as pH adjusters (e.g., an acid such as HCl), emulsifiers or dispersing agents, buffering agents, preservatives, wetting agents and gelling agents may also be present. Most preferably, the nasal composition is isotonic, i.e., it has the same osmotic pressure as blood and lacrimal fluid.

Optional Consistency Aids

Optionally, consistency aids are present at a level of from about 0.1% to about 50% by weight of the composition, preferably from about 1% to about 30%, more preferably from about 5% to about 20% by weight. These consistency aids are low molecular weight mono- and polyols and are selected from the group consisting of monosaccharides such as glucose (dextrose), fructose (levulose); disaccharides such as sucrose, lactose, maltose, cellobiose and other sugars, ribose, glycerine, sorbitol, xylitol, inositol, propylene glycol, galactose, mannose, xylose, rhamnose, glutaraldehyde, invert sugars, ethanol, honey, mannitol, polyethylene glycol, glycerol, and mixtures thereof; preferably the polyols are selected from the group consisting of honey, sorbitol, glycerine, glycerol and mixtures thereof.

These compounds provide enhanced physical stability to the present compositions. In addition these consistency aids are preferred for providing the proper consistency of the composition prior to administration so that an optimal degree of spreading over the mucosa is achieved after administration. Specifically, these consistency aids will reduce or delay the rate at which the particulates in the dispersions bridge or are adsorbed by the mucin of the mucosa. This permits the composition to better spread and coat the tissue before triggering causes the viscosity of the composition to increase.

Method of Using and Making the Composition

The compositions of the present invention can be administered per orally (the dose is swallowed), topically applied to the oral cavity (sprayed into oral cavity, sachet or general topical administration), and/or intranasally, at a safe and effective amount.

The term "pharmaceutically-acceptable", as used herein, means that the components present in the compositions of the present invention are compatible, safe, and suitable for per oral, oral, and/or intranasal administration to a human or lower animal. The term "compatible", as used herein, means that the components of the pharmaceutical compositions are capable of being commingled with each other in a manner that no interaction occurs which would substantially reduce the pharmaceutical efficacy and/or safety of the pharmaceutical compositions under ordinary use situations.

By "safe and effective amount" as used herein is meant an amount of silica, titanium dioxide, clay, or active agent, etc., high enough to significantly (positively) modify the condition to be treated or to effect the desired result, but low enough to avoid serious side effects (at a reasonable benefit/risk ratio), within the scope of sound medical/dental judgment. The safe and effective amount, will vary with the particular condition or disease being treated, the age and physical condition of the patient being treated, the severity of the condition, the duration of treatment, the nature of concurrent therapy, the specific form of the particles or active agent employed, and the particular vehicle from which the particles or active agent is applied.

The amount of the pharmaceutical mucoadhesive composition administered depends upon the percent of active ingredients and/or particulate component within its formula, such as an analgesic, decongestant, cough suppressant, expectorant, antihistamine, respiratory agent, gastrointestinal agent, etc. required per dose, stability, release characteristics and other pharmaceutical parameters.

Usually from about 0.2 mg/kg to about 500 mg/kg per day, preferably from about 1 mg/kg to about 300 mg/kg per day and most preferably from about 5 mg/kg per day to about 200 mg/kg per day of the pharmaceutical composition is administered as described herein. This amount can be given in a single dose, or, preferably, in multiple (two to six) doses per day, or given as a sustained release dosage over the course of treatment. Generally, each individual dosage of the pharmaceutical compositions of the present invention range from about 1 mg/kg to about 25 mg/kg, preferably from about 2 mg/kg to about 15 mg/kg and most preferably from about 3 mg/kg to about 10 mg/kg. While dosages higher than the foregoing may be effective, care must be taken, as with any drug, in some individuals to prevent adverse side effects.

The liquid compositions of the present invention can be administered by rinsing the oral cavity with the composition followed by either swallowing or expectorating the composition. In addition the composition can be administered intranasally, or per oral as a liquid, or sprayed into the oral cavity or sprayed on the back of the throat. In addition soft gelatin capsules (or other soft capsule) can be filled with the liquid composition of the present invention. This liquid capsule can then be chewed by the individual to release the liquid into the oral cavity, throat, and/or the alimentary canal.

Preferably the intranasal composition is applied to the nasal mucosa via topical application (spray and/or drops) of a safe and effective amount of the composition to treat nasal symptoms. The frequency of topical application to the nasal mucosa may vary, depending upon personal or medical needs, but generally ranges from about once per day to about four times daily, preferably twice daily. A typical dose contains one to four sprays per nostril.

The desired isotonicity of the intranasal compositions of this invention may be accomplished using, for example, the sodium chloride already present, or other pharmaceutically-acceptable agents such as dextrose, boric acid, citric acid, sodium tartrate, sodium phosphate, potassium phosphate, propylene glycol or other inorganic or organic solutes or mixtures thereof. Sodium chloride is preferred particularly for buffers containing sodium ions. Further examples of sodium chloride equivalents are disclosed in *Remington's*

Pharmaceutical Sciences pp. 1491–1497 (Alfonso Gennaro 18$^{th}$ ed. 1990).

When administering a dose of the composition of the present invention, it is important not to further dilute the composition with water or other liquid. Further dilution will decrease or eliminate the mucoadhesive property of the present compositions.

The liquid compositions of the present invention are made by conventional pharmaceutical practices. In preparing the liquid oral dosage forms, the active component and particulate component are incorporated into an aqueous based orally acceptable pharmaceutical carrier consistent with conventional pharmaceutical practices. As indicated above this liquid composition can be administered as is or can be incorporated into a gelatin capsule (or other soft capsule) which can be further chewed or punctured to administer the composition. Methods for preparation and manufacture of colloidal dispersions, suspensions, and/or the incorporation of these into gelatin capsules, etc. are discussed in *Remington's Pharmaceutical Sciences* 19$^{th}$ ed. 1995 Vol. II (Alfonso R. Gennaro, editor), pp. 1509–1518 and 1615–1649, incorporated herein by reference.

The following examples illustrate embodiments of the present invention wherein both essential and optional ingredients are combined. The present invention is not limited by these examples.

EXAMPLE 1

Dispersion containing bismuth subsalicylate for disorders of the stomach and intestinal tract.

| COMPONENT | % BY WT. |
|---|---|
| TiO$_2$[1] | 15 |
| Bismuth subsalicylate powder | 1.75 |
| purified water | q.s. to 100% |

[1]Uniform, spherical and uncoated on the surface and of approximately 50 nm diameter primary particle size. This can be made by a method disclosed in N. Kallay and E. Matijevic. Langmuir 1, p. 195, 1985.

Preparation

Add TiO$_2$ with stirring to water until a uniform dispersion is obtained. Add bismuth subsalicylate powder and stir for 5 minutes. Disperse entire mixture further by ultrasonic treatment to ensure complete and homogenous dispersion. Flavor, for example peppermint, and sweetener such as sodium saccharin may be added.

Use: The formulation is taken from a spoon by a person with gastritis. Administration of two tablespoons every 2 hours delivers the active agent to the stomach mucosal surface and relieves discomfort.

EXAMPLE 2

Aluminum Hydroxide Antacid with special targeting to the distal espohagus and esophageal sphincter.

| COMPONENT | % BY WT. |
|---|---|
| Dried Aluminum hydroxide gel powder antacid | 7 |
| Amorphous silica[2] (Cab-O-Sil M5) | 8.3 |
| purified water | q.s. to 100% |

[2](Cab-O-Sil M5) Available from Cabot Corporation.

Preparation

Prepare a 6% dispersion of silica in water by stirring the silica into purified water. After a uniform dispersion is obtained, add the aluminum hydroxide powder with stirring. Treat this mixture with ultrasonic energy (by this process, the silica particles which were in the form of small aggregates, are broken up and migrate to coat the aluminum hydroxide gel particles). After a uniform dispersion is obtained by sonification, add the final 2.3% of silica with gentle stirring. Flavor and sweetener may be added as desired. The Sedimentation volume ratio is 1.

Use: A person experiencing heartburn due to reflux swallows one tablespoon of the formulation every 2 hours. The heartburn discomfort will be almost immediately stopped as the antacid formulation contacts the esophageal mucosa. Some of the aluminum hydroxide antacid is held within distal esophageal region ready to neutralize any more gastric acid which might be refluxed there.

EXAMPLE 3

Sucralfate dispersion with enhanced mucosal coating and retention.

| COMPONENT | % BY WT. |
|---|---|
| Amorphous silica[3] | 6 |
| Sucralfate powder[4] | 20 |
| Sorbitol 70% solution | 20 |
| Sodium citrate dihydrate | 1.25 |
| purified water | q.s. to 100% |

[3](Cab-O-Sil M-5) Available from Cabot Corporation.
[4]Available from Katsura, Japan.

Preparation

Combine Cab-O-Sil and water and shake by hand until a uniform dispersion is obtained. Add the sorbitol and mix. Add sucralfate and mix by hand using a spatula. The formulation will be a thick paste. Add the sodium citrate dihydrate and mix again. The formulation will liquefy upon addition of the sodium citrate. Treat with ultrasonic energy until a microscopically uniform dispersion is formed. Flavor and sweetener may be added as desired.

Use: A person suffering from esophagitis swallows one teaspoon 2 times per day until the esophagitis is relieved. The sedimentation volume ratio of this formulation is 1.

EXAMPLE 4

Calcium carbonate containing antacid with improved espohageal retention.

| COMPONENT | % BY WT. |
|---|---|
| Magnesium aluminum silicate[5] | 7.5 |
| potassium bicarbonate | 0.08 |
| Calcium carbonate | 7.72 |

-continued

| COMPONENT | % BY WT. |
|---|---|
| glycerin | 5.0 |
| sorbitol 70% solution | 11 |
| sucrose | 15 |
| cooling agent TK-10 ®[6] | 0.002 |
| monobasic potassium phosphate | 0.25 |
| vanilla cream flavor | 0.06 |
| green color | 0.001 |
| benzyl alcohol | 0.20 |
| mint flavor | 0.005 |
| WS-3[7] | 0.008 |
| methyl paraben | 0.05 |
| propyl paraben | 0.01 |
| hydrogen peroxide | 0.6 |
| purified water | q.s. to 100% |

[5]Type IIA.
[6]Menthol, 3-1-menthoxy propane-1,2-diol manufactured by Takasago.
[7]N-ethyl-p-menthan-3-carboxamide.

Preparation

Mix all of the water except 2% with the magnesium aluminum silicate and stir under high shear for at least 1 hour. Add glycerin and sorbitol and mix thoroughly. Add potassium bicarbonate and calcium carbonate with vigorous stirring until a uniform consistency is reached. Add sucrose and stir to obtain a uniform consistency. Dissolve the TK-10, monobasic potassium phosphate, vanilla cream flavor, and green color in the 2% remaining water. Add to the other ingredients and mix to obtain a uniform consistency. Combine the 0.16% benzyl alcohol with the parabens and add to the other ingredients and mix to obtain a uniform consistency. Combine mint flavor, 0.04% benzyl alcohol, and WS-3, and add to the other ingredients and mix to uniform consistency. Add hydrogen peroxide and mix approximately 10 minutes. The sedimentation volume ratio of this composition is 1. The zero shear viscosity is 256,800 pascal seconds. The triggered viscosity ratio is 2.37, and the high shear viscosity, at 100 per seconds, is 0.848 pascal seconds. The percent retained after 30 rinses in saliva by the method discussed above is 90.3%.

Use: One or 2 tablespoons is swallowed by a person experiencing heartburn. Generally, only one administration will be needed to relieve the heartburn pain, and relief will be very rapid.

EXAMPLE 5

Bismuth subsalicylate containing liquid with improved esophageal retention for heartburn.

| COMPONENT | % BY WT. |
|---|---|
| Magnesium aluminum silicate[8] | 6.04 |
| Bismuth subsalicylate | 1.75 |
| Methyl salicylate | 0.089 |
| salicylic acid | 0.071 |
| sodium saccharin | 0.061 |
| sodium salicylate | 0.060 |
| sodium benzoate | 0.025 |
| sorbic acid | 0.13 |
| purified water | q.s. to 100% |
| color as desired | |

[8]Type IIA.

Preparation

Mix all of the water except 2% with the magnesium aluminum silicate and stir under high shear for at least 1 hour to fully hydrate. Add bismuth subsalicylate and stir for 10 minutes. Disperse with ultrasonic energy for 20 minutes. Separately, dissolve all other components in the remaining 2% of the water. Add to the magnesium aluminum silicate/bismuth dispersion and stir for 15 minutes. Adjust pH to approximately 4.2. The sedimentation volume ratio is 1. The zero shear viscosity is 1,090,000 pascal seconds. The triggered viscosity ratio is 1.26, and the high shear viscosity, at 100 per seconds, is 0.705 pascal seconds. The percent retained after 30 rinses in saliva by the method discussed above is 94.8%.

Use: One tablespoon is taken by a person experiencing heartburn, as soon as possible after the discomfort begins. Relief of the heartburn is almost immediate, and a palliative coating layer is retained in the esophagus to prevent other reflux events over the next several hours from causing more pain.

EXAMPLE 6

Demulcent vehicle for treatment of sore throat and cough.

| COMPONENT | % BY WT. A | % BY WT. B |
|---|---|---|
| Ethanol | 4.31 | 5 |
| Dextromethorphan hydrobromide | 0.15 | 0.10 |
| glyceryl guaicolate | — | 1.33 |
| propylene glycol | 8.62 | 10 |
| polyoxyl 40 stearate | 0.26 | 0.13 |
| sodium citrate dihydrate | 0.225 | 0.112 |
| citric acid | 0.146 | 0.073 |
| sodium benzoate | 0.086 | 0.086 |
| natural menthol | 0.030 | 0.045 |
| oil of eucalyptus | 0.018 | 0.025 |
| sucralose | — | 0.10 |
| TK-10 ®[9] | 0.017 | — |
| sodium saccharin | 0.10 | 0.10 |
| natural honey | 13 | 3.5 |
| magnesium aluminum silicate clay[10] | 3.75 | 4.15 |
| flavor and color | as desired | as desired |
| purified water | q.s. to 100% | q.s. to 100% |

[9]Menthol, 3-1-menthoxy propane-1,2-diol manufactured by Takasago.
[10]Type IIA.

Preparation

Mix all of the water with the magnesium aluminum silicate and stir under high shear for at least 1 hour to fully hydrate. Add polyoxyl 40 stearate, citric acid, sodium citrate, sodium benzoate, and sodium saccharin to the magnesium aluminum silicate dispersion. Separately, combine the ethanol and propylene glycol and mix. Add menthol, oil of eucalyptus, TK 10, and dextromethorphan to the ethanol/propylene glycol mix. Add the ethanol/propylene glycol solution to the main vessel with magnesium aluminum silicate and mix. Add the honey, flavor and color and mix for 10 minutes. Add the glyceryl guaicolate as a finely ground powder in the final step and mix for at least 10 minutes. The sedimentation volume ratio is greater than about 0.98. The zero shear viscosity is 55,400 pascal seconds. The triggered viscosity ratio is 1.33, and the high shear viscosity, at 100 per seconds, is 0.282 pascal seconds.

Use: When 15 cc of the above composition is administered by spoon to a person with a cough or sore throat, the liquid spreads on the throat, and provides a soothing coating to minimize sore throat pain and cough. The soothing material is felt in the throat for at least 1 hour and is not washed away by drinking liquid beverages. The formulation also provides an effective amount of antisussive medication, dextromethorphan hydrobromide. A person with a productive, wet cough swallows 15 cc of composition B. A combination of the demulcent properties of the vehicle and the action of the glyceryl guaicolate expectorant provides an enhanced ability to clear the mucus. A soothing action in the throat is also obtained, and an effective amount of the antitussive agent dextromethorphan is delivered systemically. The antitussive medication of Example 6 can be substituted with diphenhydramine, codeine, hydrocodone, and hydromorphone.

EXAMPLE 7

Demulcent and soothing vehicle for soothing of a sore throat irritated by cough, and providing prolonged delivery of aromatic menthol for treatment of the cough by inhalation.

| COMPONENT | % BY WT. A | % BY WT. B |
| --- | --- | --- |
| Ethanol | 4.31 | 4.3 |
| propylene glycol | 8.62 | 8.6 |
| polyoxyl stearate | 0.012 | — |
| sodium citrate dihydrate | 0.112 | 0.066 |
| citric acid | 0.073 | 0.037 |
| sodium benzoate | 0.086 | 0.086 |
| natural menthol | 1.00 | 0.8 |
| benzocaine | 2.00 | 1.0 |
| oil of eucalyptus | 0.005 | 0.004 |
| oil of sage | — | 0.14 |
| sodium saccharin | 0.10 | 0.10 |
| sucralose | — | 0.10 |
| acesulfame potassium | 0.075 | — |
| colloidal fumed silica (Cab-O-Sil M5) | 5.0 | 6.75 |
| purified water | q.s. to 100% | q.s. to 100% |

Preparation

Mix the ethyl alcohol USP and propylene glycol in a separate vessel. Add menthol and eucalyptus oil and mix to clear solution (co-solvent solution). Place the water into a separate mixing vessel. Add all other ingredients except the co-solvent solution and the silica, and stir to dissolve. Add the co-solvent solution to the water solution. Mix. Slowly add the silica with moderate mixing from a propeller type mixer. After all of the silica is added, continue mixing an additional 5–10 minutes. Over mixing, or using too high an intensity such as might be achieved with a high shear mixer, will cause the product to be too thin and have poor viscosity stability. Degas with mixing to remove air bubbles.

Use: Because of the remarkable combination of high viscosity when at rest, but dramatic shear thinning upon high shear, the formulation is able to be atomized and applied as a fine spray coating onto the back of the throat. The product is filled into a manually operated atomization pump and bottle fitted with a stem which is designed to depress the tongue and concurrently direct the atomized dispersion over the tongue and into the back of the throat (the Mistette Mark II fitted with long throat adaptor by CalMar-Albert GmbH). Five actuations applied to the back of the throat of a person with a cough secondary to a cold or flu, and/or a painful and swollen throat, will deliver 1 ml of the dispersion onto the affected area. Most of the formulation will be retained in the throat and pharyngeal region instead of being swallowed. The 5 mg of menthol in the formulation will be volatized with each breath as it passes over the therapeutic coating, and be drawn into the lungs where it soothes the coughing reflex. In the above example, benzocaine can be substituted with local anesthestics, such as lidocaine and dibucaine.

These compositions can be used alternatively as a mouthrinse wherein a subject rinses and gargles in his/her mouth with 15 ml for about 30 seconds and thereafter expectorates.

EXAMPLE 8

Breath freshening mouth rinse with soothing feel and prolonged action.

| COMPONENT | % BY WT A | % BY WT B |
| --- | --- | --- |
| Ethanol | 10.0 | 12 |
| glycerine | 10.0 | 7.5 |
| propylene glycol | 5.00 | 4 |
| methyl salicylate | 0.035 | 0.5 |
| menthol | 0.026 | 0.15 |
| eucalyptol | 0.054 | 0.12 |
| thymol | 0.039 | 0.95 |
| sodium lauryl sulfate | 0.005 | 0.006 |
| sodium benzoate | 0.086 | — |
| sodium saccharin | — | 0.08 |
| Colloidal fumed silica (Cabosil M5) | 3.50 | — |
| magnesium aluminum silicate | — | 4.65 |
| purified water | q.s. to 100% | q.s. to 100% |

Preparation

Composition A

1.) Mix ethanol, propylene glycol, and glycerine. Dissolve methyl salicylate, thymol, eucalpytol, and menthol in this solvent mixture.

2.) Separately, disperse Cabosil in water with moderate mixing from a propeller type mixer. After all of the silica is added, continue mixing an additional 5–10 minutes. Over mixing, or using too high an intensity such as might be achieved with a high shear mixer, will cause the product to be too thin and have poor viscosity stability. Add the sodium benzoate to the silica dispersion and dissolve with gentle mixing.

3.) Pour all of the solvent solution from step 1 into the silica dispersion. Briefly degas with mixing to remove air bubbles.

Composition B

1.) Mix all of the water with the clay and stir under high shear for at least 1 hour to fully hydrate the clay.

2.) In a separate vessel, combine ethanol, propylene glycol, and glycerine, and mix. Add menthol, eucalyptol, and thymol to this solvent mixture and stir for at least 10 minutes, with the vessel covered.

3.) Add the cosolvent mixture with aromatic components to the hydrated clay and mix with gentle stirring at least 5 minutes. Add methyl salicylate, saccharin, and sodium lauryl sulfate and mix with low agitation for an additional 15 minutes.

Use: Ten to 20 ml of the rinse is placed into the mouth and swished thoroughly for 30 seconds before expectorating. Odor-causing materials are effectively removed from the mouth and a pleasing layer of breath-freshening agents are retained in a thin layer inside of the mouth and on the tongue.

EXAMPLE 9
Oral analgesic throat syrup.

| COMPONENT | % BY WT. |
|---|---|
| Ethanol | 10.0 |
| propylene glycol | 5.00 |
| natural honey | 11.5 |
| Titanium dioxide[11] | 12.5 |
| menthol | 0.15 |
| lemon flavor | 0.10 |
| sodium citrate dihydrate | 0.225 |
| citric acid | 0.146 |
| sodium benzoate | 0.085 |
| purified water | q.s. to 100% |

[11]Uniform, spherical and un-coated on the surface and of approximately 50 nm diameter primary particle size. This can be made by a method disclosed in N. Kallay and E. Matijevic. Langmuir 1, p. 195, 1985.

Preparation

Menthol and lemon flavor are dissolved in a mixture of propylene glycol and ethanol. Separately, the titanium dioxide is dispersed in purified water using moderate mixing from a propellor-type mixer. The remaining ingredients are added to the titanium dioxide/water dispersion, and gentle mixing is continued to dissolve ingredients. Lastly, the menthol solution in ethanol and propylene glycol is added to the aqueous fraction and mixing is continued as before for approximately 10 minutes.

Use: A person with a sore and inflamed throat administers one teaspoon every hour to sooth the inflamed tissue.

In the above example menthol can be substituted with NSAIDs listed under analgesics above.

EXAMPLE 10
Mucoretentive Intransal Spray Decongestant

| COMPONENT | % BY WT. A | % BY WT. B | % BY WT. C |
|---|---|---|---|
| magnesium aluminum silicate, type IIA | 3.1 | — | — |
| colloidal fumed silica (Cabosil M5) | — | 7.6 | — |
| oxymetazoline hydrochloride | 0.05 | 0.05 | 0.05 |
| titanium dioxide[12] | — | — | 6.8 |
| tyloxapol | 0.15 | 0.035 | 0.035 |
| dibasic sodium phosphate | 0.04 | 0.02 | 0.02 |
| monobasic potassium phosphate | 0.13 | 0.065 | 0.065 |
| xanthan gum | — | — | 0.025 |
| benzalkonium chloride | 0.04 | 0.04 | 0.04 |
| chlorhexidine gluconate | 0.26 | 0.26 | 0.26 |
| disodium EDTA | 0.01 | 0.01 | 0.01 |
| purified water | q.s. to 100% | q.s. to 100% | q.s. to 100% |

[12]Uniform, spherical and un-coated on the surface and of approximately 50 nm diameter primary particle size. This can be made by a method disclosed in N. Kallay and E. Matijevic. Langmuir 1, p. 195, 1985.

Preparation

Composition A

Disperse the clay in one half of the total water by high shear mixing for at least 1 hour. Dissolve all other ingredients in chilled water by stirring. Filter this solution through a cellulose acetate membrane filter. Combine the filtered solution with the clay dispersion and stir for at least 10 minutes. Add flavor in an appropriate amount to provide a pleasant taste. Add camphor and eucalyptol in an appropriate amount to provide pleasant scent in use. Fill this final mixture into manually operated nasal spray pump bottles.

Composition B

Disperse the silica in the water with gentle stirring for at least 10 minutes. Add all other components except tyloxapol and gently stir an additional 10 minutes. Add tyloxapol and stir for at least 20 minutes, again ensuring that stirring is gentle.

Composition C

Disperse the xanthan gum in the water with moderate stirring for at least 30 minutes. Add the titanium dioxide and mix vigorously for 1 minute, then continue mixing gently for 10 minutes. Add all other components except tyloxapol and stir an additional 10 minutes with moderate mixing. Add tyloxapol and stir for at least 20 minutes with gentle stirring, taking care not to entrain air in the formulation.

Use: A subject with congestion sprays 5 to 500 microliters of either of the above solutions into each nostril 3 times daily. The flow properties and triggering of the formulation with the mucus lining in the nasal passage causes the formulation and active, oxymetazoline, to be retained within the region of the inflamed nasal turbinates, providing a more prolonged decongesting effect on the intranasal blood vessels.

What is claimed is:

1. A per oral or oral mucoretentive, aqueous liquid, pharmaceutical composition comprising:
    (a) from about 2% to about 50%, by weight of the composition, of colloidal particles of titanium dioxide; and
    (b) a safe and effective amount of a pharmaceutical active selected from the group consisting of gastrointestinal agents, analgesics, decongestants, expectorants, antitussives, antihistamines, bronchodilators, topical anesthetics, sensory agents, oral care agents, miscellaneous respiratory agents, and mixtures thereof;

wherein the composition has a sedimentation volume ratio of greater than about 0.90 when measured after about 48 hours, a triggered viscosity ratio of at least about 1.2; wherein the gastrointestinal agent is selected from the group consisting of anticholinergics, H2-receptor antagonists, laxatives, gastroprotectants, gastrokinetic and prokinetic agents, proton pump inhibitors, antidiarrheals, agents effective for the treatment of *H. pylori,* polyanionic agents, plant extracts effective for the treatment of gastrointestinal disorders, and mixtures thereof.

2. The composition of claim 1 wherein the composition has a sedimentation volume ratio of greater than about 0.95, when measured after about 48 hours.

3. The composition of claim 2 wherein the composition has a sedimentation volume ratio of greater than about 0.98, when measured after about 48 hours.

4. The composition of claim 1 wherein the composition has a triggered viscosity ratio of at least about 1.4.

5. The composition of claim 4 wherein the composition has a triggered viscosity ratio of at least about 1.5.

6. The composition of claim 1 wherein the level of titanium dioxide is from about 3% to about 15%, by weight of the composition.

7. The composition of claim 6 wherein the titanium dioxide has a mean particle size of less than about 1 micron.

8. The composition of claim 1 wherein the composition has a zero shear viscosity of greater than about 2,000 pascal seconds.

9. The composition of claim 8 wherein the composition has a zero shear viscosity of greater than about 7,500 pascal seconds.

10. An intranasal mucoretentive, aqueous liquid, pharmaceutical composition comprising:

(a) from about 2% to about 50%, by weight of the composition, of colloidal particles of titanium dioxide; and (b) a safe and effective amount of a pharmaceutical active selected from the group consisting of gastrointestinal agents, analgesics, decongestants, expectorants, antitussives, antihistamines, bronchodilators, topical anesthetics, sensory agents, oral care agents, miscellaneous respiratory agents, and mixtures thereof;

wherein the composition has a sedimentation volume ratio of greater than about 0.90 when measured after about 48 hours and a triggered viscosity ratio of at least about 1.2.

11. The composition of claim 10 wherein the composition has a sedimentation volume ratio of greater than about 0.95, when measured after about 48 hours.

12. The composition of claim 11 wherein the composition has a sedimentation volume ratio of greater than about 0.98, when measured after about 48 hours.

13. The composition of claim 10 wherein the composition has a triggered viscosity ratio of at least about 1.4.

14. The composition of claim 13 wherein the composition has a triggered viscosity ratio of at least about 1.5.

15. The composition of claim 10 wherein the level of silica is from about 3% to about 15%, by weight of the composition.

16. The composition of claim 10 wherein the titanium dioxide has a mean particle size of less than about 1 micron.

17. The composition of claim 10 wherein the composition has a zero shear viscosity of greater than about 2,000 pascal seconds.

18. The composition of claim 17 wherein the composition has a zero shear viscosity of greater than about 7,500 pascal seconds.

19. A method of coating the alimentary canal by administering a safe and effective amount of the composition of claim 1.

20. A method of coating the nasal mucosa by administering a safe and effective amount of the composition of claim 10.

21. A method of preventing or treating symptoms of upper respiratory tract infections or upper respiratory tract tissue irritation or damage, by administering a safe and effective amount of the composition of claim 1.

22. A method of preventing or treating symptoms of upper respiratory tract infections or upper respiratory tract tissue irritation or damage, by administering a safe and effective amount of the composition of claim 10.

23. A method of administering an active agent to the alimentary canal by administering a safe and effective amount of the composition of claim 1.

24. A method of administering an active agent to the nasal mucosa by administering a safe and effective amount of the composition of claim 10.

* * * * *